United States Patent
Kramer

(10) Patent No.: US 11,453,630 B2
(45) Date of Patent: Sep. 27, 2022

(54) CATALYST AND PROCESS FOR OXYCHLORINATION OF ETHYLENE TO DICHLOROETHANE

(71) Applicant: Oxy Vinyls, LP, Dallas, TX (US)

(72) Inventor: Keith Kramer, Andover, KS (US)

(73) Assignee: Oxy Vinyls, LP, Dallas, TX (US)

(*) Notice: Subject to any disclaimer, the term of this patent is extended or adjusted under 35 U.S.C. 154(b) by 116 days.

(21) Appl. No.: 15/321,770

(22) PCT Filed: Jun. 23, 2015

(86) PCT No.: PCT/US2015/037104
§ 371 (c)(1),
(2) Date: Dec. 23, 2016

(87) PCT Pub. No.: WO2015/200270
PCT Pub. Date: Dec. 30, 2015

(65) Prior Publication Data
US 2017/0137351 A1    May 18, 2017

Related U.S. Application Data

(60) Provisional application No. 62/015,732, filed on Jun. 23, 2014.

(51) Int. Cl.
| | | |
|---|---|---|
| *C07C 17/156* | (2006.01) | |
| *C07C 19/045* | (2006.01) | |
| *B01J 21/04* | (2006.01) | |
| *B01J 23/889* | (2006.01) | |
| *B01J 23/72* | (2006.01) | |
| *B01J 23/78* | (2006.01) | |
| *B01J 35/10* | (2006.01) | |
| *B01J 37/02* | (2006.01) | |
| *B01J 35/02* | (2006.01) | |
| *B01J 35/00* | (2006.01) | |

(52) U.S. Cl.
CPC ............ *C07C 17/156* (2013.01); *B01J 21/04* (2013.01); *B01J 23/72* (2013.01); *B01J 23/78* (2013.01); *B01J 23/8892* (2013.01); *B01J 35/0006* (2013.01); *B01J 35/023* (2013.01); *B01J 35/1019* (2013.01); *B01J 35/1038* (2013.01); *B01J 35/1042* (2013.01); *B01J 37/0201* (2013.01); *B01J 37/024* (2013.01)

(58) Field of Classification Search
None
See application file for complete search history.

(56) References Cited

U.S. PATENT DOCUMENTS

| | | | |
|---|---|---|---|
| 4,329,527 A | 5/1982 | Kuhn et al. | |
| 2004/0192978 A1 | 9/2004 | Casagrande et al. | |
| 2009/0054708 A1 | 2/2009 | Van Rooijen et al. | |
| 2014/0128643 A1* | 5/2014 | Tompers | C07C 17/156 570/243 |

FOREIGN PATENT DOCUMENTS

| | | |
|---|---|---|
| EP | 1666145 A1 | 6/2006 |
| JP | S56-092828 A | 7/1981 |
| JP | 2004-298871 A | 10/2004 |
| JP | 2009-504711 A | 2/2009 |
| WO | 8101284 A1 | 5/1981 |
| WO | 2014071423 A1 | 5/2014 |

OTHER PUBLICATIONS

International Search Report and Written Opinion for Appl. No. PCT/US2015/037104 dated Sep. 7, 2015, pp. 1-12.

* cited by examiner

*Primary Examiner* — Medhanit W Bahta
(74) *Attorney, Agent, or Firm* — Renner, Kenner; Arthur M. Reginelli

(57) ABSTRACT

In an oxychlorination process of the type where ethylene is converted to 1,2-dichloroethane in the presence of a supported copper catalyst, the improvement comprising: the use of a supported catalyst prepared by (i) impregnating, within a first step, an alumina support with a first aqueous solution including copper, to thereby form a first catalyst component; and (ii) impregnating, within a subsequent step, the first catalyst component with a second aqueous solution including copper and alkaline earth metal, to thereby form the supported catalyst.

15 Claims, No Drawings

CATALYST AND PROCESS FOR OXYCHLORINATION OF ETHYLENE TO DICHLOROETHANE

This Application is a National-Stage application of PCT/US2015/037104 filed on Jun. 23, 2015, which claims the benefit of U.S. Provisional Application Ser. No. 62/015,732, filed on Jun. 23, 2014, which are incorporated herein by reference.

FIELD OF THE INVENTION

Embodiments of the invention relate to catalysts for oxychlorination of ethylene to dichloroethane. The catalysts advantageously exhibit less stickiness, especially at high copper loadings, and they are therefore advantageously useful in baffled-bed reactors.

BACKGROUND OF THE INVENTION

Oxychlorination is the process where ethylene is converted to 1,2-dichloroethane. This reaction can take place in a vapor phase reaction over a fluidized catalyst bed in a mixture of ethylene, hydrogen chloride, and oxygen (e.g. pure oxygen or air). Copper catalysts supported on alumina supports are well known in the art of oxychlorination catalysts. For example, U.S. Pat. No. 5,292,703 teaches a catalyst for oxychlorination of ethylene to produce 1,2-dichloroethane, where the catalyst includes copper chloride, at least one alkali metal, at least one transition metal, and at least one Group IIA (i.e. alkaline earth metal) metal on a support such alumina. This catalyst purportedly results in high percent ethylene efficiency, high dichloroethane product purity, and high percent HCl conversion without exhibiting catalyst stickiness. As the skilled person understands, catalyst stickiness refers to an agglomeration of catalyst particles and can deleteriously impact ethylene and hydrogen chloride feedstock efficiencies in a fluid bed oxychlorination process.

U.S. Publ. No. 2009/0054708 discloses an oxychlorination catalyst that is designed for use in a baffled bed reactor. The catalyst includes 5.5 to 14 wt % copper, alkaline earth metal, alkali metal, and transition metal, with the limitation that the amount of alkali metal is no higher than 1 wt %. The reference discloses that it has been found that significant levels of alkali metal in the catalyst increases susceptibility to stickiness.

SUMMARY OF THE INVENTION

Embodiments of the invention provide an oxychlorination process of the type where ethylene is converted to 1,2-dichloroethane in the presence of a supported copper catalyst, the improvement comprising: the use of a supported catalyst prepared by (i) impregnating, within a first step, an alumina support with a first aqueous solution including copper and a transition metal to thereby form a first catalyst component; and (ii) impregnating, within a subsequent step, the first catalyst component with a second aqueous solution including copper and alkaline earth metal to thereby form the supported catalyst.

Other embodiments of the invention provide a process for producing a catalyst for the oxychlorination of ethylene to 1,2-dichloroethane, the process comprising the steps of impregnating, within a first step, an alumina support with a first aqueous solution including copper and a transition metal to thereby form a first catalyst component and impregnating, within a subsequent step, the first catalyst component with a second aqueous solution including copper and alkaline earth metal, to thereby form the supported catalyst.

Other embodiments of the invention provide an oxychlorination process comprising the step of converting ethylene to 1,2-dichloroethane in the presence of a catalyst, oxygen, and hydrogen chloride, where the catalyst is produced by: (i) impregnating, within a first step, an alumina support with a first aqueous solution including copper and a transition metal, to thereby form a first catalyst component; and (ii) impregnating, within a subsequent step, the first catalyst component with a second aqueous solution including copper and alkaline earth metal, to thereby form the supported catalyst.

DETAILED DESCRIPTION OF ILLUSTRATIVE EMBODIMENTS

Embodiments of the invention are based, at least in part, on the discovery of a supported catalyst for oxychlorination of ethylene to dichloroethane including copper, alkali metal, alkaline earth metal, and optionally transition metal. It has unexpectedly been discovered that the techniques employed to fabricate the supported catalyst, especially the techniques employed to impregnate the support with the various metals, impacts catalyst stickiness, especially at relatively high copper loadings. Thus, the fabrication techniques can be manipulated, especially with regard to the alkali metal and alkaline earth metal, to produce technologically useful supported catalysts that do not deleteriously suffer from stickiness. Moreover, while the prior art suggests that alkali metals at greater than 1 wt % have a deleterious impact on stickiness and negligible impact and catalyst efficiency, it has been found that the presence of alkali metal at levels greater than 1 wt % can be advantageous without deleteriously impacting stickiness, and therefore certain embodiments include supported catalyst with greater than 1 wt % alkali metal. In one or more embodiments, the supported catalyst is advantageously useful in baffled bed reactors. Also, in one or more embodiments, the catalyst compositions advantageously can be used in an oxychlorination process to yield higher HCl conversion, lower chlorinated by-byproducts, and/or lower oxidation by-products. Still further, the catalyst composition may advantageously be used in an oxychlorination process that can operate at relatively high temperatures without producing deleterious levels of carbon oxides.

Catalyst Composition

In one or more embodiments, the catalyst composition, which may also be referred to as a supported catalyst, includes an active catalyst metal, catalyst promoters, and a catalyst support. As will be described in greater detail below, the catalyst composition may be prepared by impregnating the support with aqueous solutions carrying one or more of the active catalyst metal and catalyst promoters by a method commonly known as incipient wetness impregnation.

In one or more embodiments, the active catalyst metal includes copper in the form of copper salts. In one or more embodiments, useful copper salts include, but are not limited to, copper (II) halides such as copper (II) chlorides. Practice of one or more embodiments of the present invention is not, however, limited by the selection of any particular copper salt, and therefore reference can be made to U.S. Pat. No. 5,292,703 and U.S. Publ. No. 2009/0054708, which are incorporated herein by reference.

As will be explained in greater detail below, the catalyst composition is described based upon weight percentages.

The composition can also be described based upon moles per kilogram catalyst, which the skilled person can easily calculate. Nonetheless, for ease of description, the weight percentages described herein are provided in moles per kilogram catalyst within the tables herein. Those skilled in the art will appreciate that the moles per kilogram catalyst provided in the table below are applicable to any disclosure of weight for the purpose of this specification.

In one or more embodiments, the catalyst composition includes greater than 5.0, in other embodiments greater than 6.0, in other embodiments greater than 7.0, and in other embodiments greater than 8.0 wt % copper metal based upon the entire weight of the catalyst composition, which as described above includes the catalyst support, metals, and ligands or counter anions associated with any given metal additive. In these or other embodiments, the catalyst composition includes less than 12, in other embodiments less than 11, in other embodiments less than 10, and in other embodiments less than 9 wt % copper metal based upon the entire weight of the catalyst composition. In one or more embodiments, the catalyst composition includes from about 5.0 to about 12, in other embodiments from about 6.0 to about 11, in other embodiments from about 7.0 to about 10.5, and in other embodiments from about 8.0 to about 10.0 wt % copper metal based upon the entire weight of the catalyst composition.

In one or more embodiments, a catalyst promoter or complementary metal includes alkali metal in the form of alkali metal salts. In one or more embodiments, useful alkali metal salts include, but are not limited to, halides of lithium, sodium, and potassium. In particular embodiments, potassium chloride is employed. Practice of one or more embodiments of the present invention is not, however, limited by the selection of any particular alkali metal salt, and therefore reference can be made to U.S. Pat. No. 5,292,703 and U.S. Publ. No. 2009/0054708, which are incorporated herein by reference.

In one or more embodiments, the catalyst composition includes greater than 0.25, in other embodiments greater than 0.5, in other embodiments greater than 1.0, and in other embodiments greater than 1.05 wt % alkali metal based upon the entire weight of the catalyst composition, which as described above includes the catalyst support, metals, and ligands or counter anions associated with any given metal additive. In these or other embodiments, the catalyst composition includes less than 1.6, in other embodiments less than 1.5, in other embodiments less than 1.4, and in other embodiments less than 1.3 wt % alkali metal based upon the entire weight of the catalyst composition. In one or more embodiments, the catalyst composition includes from about 0.25 to about 1.6, in other embodiments from about 0.5 to about 1.5, in other embodiments from about 1.0 to about 1.4, and in other embodiments from about 1.05 to about 1.3 wt % alkali metal based upon the entire weight of the catalyst composition. The foregoing wt % s are based upon the use of potassium as the alkali metal; where another alkali metal is substituted for the potassium, the foregoing wt % (s) will be adjusted for the difference in elemental weight of the different alkali metal, keeping a molar equivalent to the moles of potassium present in any given wt %.

In one or more embodiments, a catalyst promoter or complementary metal includes alkaline earth metal in the form of alkaline earth metal salts. In one or more embodiments, useful alkaline earth metal salts include, but are not limited to, halides of beryllium, magnesium, and calcium. In particular embodiments, magnesium dichloride is employed. Practice of one or more embodiments of the present invention is not, however, limited by the selection of any particular alkaline earth metal salt, and therefore reference can be made to U.S. Pat. No. 5,292,703 and U.S. Publ. No. 2009/0054708, which are incorporated herein by reference.

In one or more embodiments, the catalyst composition includes greater than 0.25, in other embodiments greater than 0.5, in other embodiments greater than 0.75, and in other embodiments greater than 1.0 wt % alkaline earth metal based upon the entire weight of the catalyst composition, which as described above includes the catalyst support, metals, and ligands or counter anions associated with any given metal additive. In these or other embodiments, the catalyst composition includes less than 3.0, in other embodiments less than 2.5, in other embodiments less than 2.25, and in other embodiments less than 2.0 wt % alkaline earth metal based upon the entire weight of the catalyst composition. In one or more embodiments, the catalyst composition includes from about 0.25 to about 3.0, in other embodiments from about 0.5 to about 2.5, in other embodiments from about 0.75 to about 2.25, and in other embodiments from about 1.0 to about 2.0 wt % alkaline earth metal based upon the entire weight of the catalyst composition. The foregoing wt % (s) are based upon the use of magnesium as the alkaline earth metal; where another alkaline earth metal is substituted for the magnesium, the foregoing wt % (s) will be adjusted for the difference in elemental weight of the different alkaline earth metal, keeping a molar equivalent to the moles of magnesium present in any given wt %.

In one or more embodiments, a catalyst promoter or complementary metal includes transition metal in the form of transition metal salts. In one or more embodiments, useful transition metal salts include, but are not limited to, halides of manganese or rhenium. In particular embodiments, manganese and/or rhenium chlorides are employed. Practice of one or more embodiments of the present invention is not, however, limited by the selection of any particular transition metal salt, and therefore reference can be made to U.S. Pat. No. 5,292,703 and U.S. Publ. No. 2009/0054708, which are incorporated herein by reference.

In one or more embodiments, the catalyst composition includes greater than 0, in other embodiments greater than 0.5, in other embodiments greater than 0.75, and in other embodiments greater than 1.0 wt % transition metal based upon the entire weight of the catalyst composition, which as described above includes the catalyst support, metals, and ligands or counter anions associated with any given metal additive. In these or other embodiments, the catalyst composition includes less than 3.0, in other embodiments less than 2.5, in other embodiments less than 2.3, in other embodiments less than 2.2, and in other embodiments less than 2.0 wt % transition metal based upon the entire weight of the catalyst composition. In one or more embodiments, the catalyst composition includes from about 0 to about 2.5, in other embodiments from about 0.75 to about 2.3, and in other embodiments from about 1.0 to about 2.2 wt % transition metal based upon the entire weight of the catalyst composition. The foregoing wt % (s) are based upon the use of manganese as the transition metal; where another transition metal is substituted for the manganese, the foregoing wt % (s) will be adjusted for the difference in elemental weight of the different transition metal, keeping a molar equivalent to the moles of manganese present in any given wt %.

Support Materials

Practice of one or more embodiments of the present invention are limited by the selection of any particular catalyst support. In this regard, U.S. Pat. No. 5,292,703 and U.S. Publ. Nos. 2009/0054708, 2009/0298682, 2010/0274061, 2006/0129008, and 2004/0192978 are incorporated herein by reference.

In particular embodiments, alumina supports are employed. Alumina supports useful in oxychlorination catalysts are well known in the art and commercially available under the tradenames Catalox and Puralox (Sasol).

Preparation of Catalyst Materials

As suggested above, the supported catalyst materials of the present invention may be prepared by impregnating the support with aqueous solutions carrying one or more of the active catalyst metal and catalyst promoters by incipient wetness impregnation. For purposes of this specification, and unless otherwise stated, the technique of impregnating the support should be understood in its broadest sense and includes wetting the support over a wide range (e.g. 80% to 115% of its pore volume). In one or more embodiments, the support treated with the aqueous solution, which becomes wetted, can be subsequently dried. In one or more embodiments, the supported catalyst or any precursor can be calcined.

In one or more embodiments, the step of impregnating the support takes place in multiple steps. In other words, the support is impregnated in two or more impregnation steps to produce the desired supported material. In one or more embodiments, a two-step impregnation process is employed using first and second aqueous solutions containing copper salts and specific promoter metals. As used herein, reference to the first impregnation step will correspond to the use of the first aqueous solution, and reference to a second impregnation step will correspond to the use of the second aqueous solution.

In one or more embodiments, the two impregnation steps are performed using standard techniques for multiple impregnations of a catalyst support. In one or more embodiments, after the first impregnation step, the catalyst may be dried prior to the second impregnation step. In one or more embodiments, the catalyst material is dried to a point where it includes less than 5.0%, in other embodiments less than 3.0%, and in other embodiments less than 1.0% water on a weight basis before the second impregnation step. In one or more embodiments, the catalyst material is dried after the first impregnation step to a level where sufficient pore volume is achieved so as to allow the second impregnation step to deposit the desired amount of material. Following the second impregnation step, the catalyst material is again dried. In one or more embodiments, after the second impregnation step, the catalyst material is dried to a point where it includes less than 5.0%, in other embodiments less than 3.0%, and in other embodiments less than 1.0% water on a weight basis.

First Solution

In one or more embodiments, the first solution includes a copper salt, an alkali metal salt, optionally an alkaline earth metal salt, and optionally a transition metal salt. In particular embodiments, the first solution includes a copper salt, an alkali metal salt, and an alkaline earth metal salt. And, in particular embodiments, the first solution includes a copper salt, an alkali metal salt, an alkaline earth metal salt, and a transition metal salt.

In one or more embodiments, the concentration of the copper salt within the first solution is calculated to provide the support, after drying, with a copper metal concentration of greater than 2.5, in other embodiments greater than 3.3, in other embodiments greater than 3.7, and in other embodiments greater than 4.0 wt % copper metal based upon the entire weight of the catalyst composition, which as described above includes the catalyst support, metals, and ligands or counter anions associated with any given metal additive. In these or other embodiments, the concentration of the copper salt within the first solution is calculated to provide the support, after drying, with a copper metal concentration of less than 6.5, in other embodiments less than 5.5, and in other embodiments less than 5.0 wt % copper metal based upon the entire weight of the catalyst composition. In one or more embodiments, the concentration of the copper salt within the first solution is calculated to provide the support, after drying, with a copper metal concentration of about 2.5 to about 6, in other embodiments from about 3.3 to about 5.5, and in other embodiments from about 4.0 to about 5.0 wt % copper metal based upon the entire weight of the catalyst composition. Stated another way, the foregoing represent the wt % (s) copper on the dried support following the first impregnation step.

In one or more embodiments, the concentration of the alkali metal salt within the first solution is calculated to provide the support, after drying, with a alkali metal concentration of greater than 0.25, in other embodiments greater than 0.5, in other embodiments greater than 1.0, and in other embodiments greater than 1.05 wt % alkali metal based upon the entire weight of the catalyst composition, which as described above includes the catalyst support, metals, and ligands or counter anions associated with any given metal additive. In these or other embodiments, the concentration of the alkali metal salt within the first solution is calculated to provide the support, after drying, with an alkali metal concentration of less than 1.6, in other embodiments less than 1.5, in other embodiments less than 1.4, and in other embodiments less than 1.3 wt % alkali metal based upon the entire weight of the catalyst composition. In one or more embodiments, the concentration of the alkali metal salt within the first solution is calculated to provide the support, after drying, with an alkali metal concentration of from about 0.25 to about 1.6, in other embodiments from about 0.5 to about 1.5, in other embodiments from about 1.0 to about 1.4, in other embodiments from about 1.05 to about 1.3 wt % alkali metal based upon the entire weight of the catalyst composition. The foregoing wt % (s) are based upon the use of potassium as the alkali metal; where another alkali metal is substituted for the potassium, the foregoing wt % (s) will be adjusted for the difference in elemental weight of the different alkali metal, keeping a molar equivalent to the moles of potassium present in any given wt %. Stated another way, the foregoing represent the wt % (s) alkali metal on the dried support following the first impregnation step.

In one or more embodiments, the concentration of the alkaline earth salt within the first solution is calculated to provide the support, after drying, with a alkaline earth metal concentration of greater than 0.5, in other embodiments greater than 0.7, and in other embodiments greater than 0.85, and in other embodiments greater than 1.0 wt % alkaline earth metal based upon the entire weight of the catalyst composition, which as described above includes the catalyst support, metals, and ligands or counter anions associated with any given metal additive. In these or other embodiments, the concentration of the alkaline earth salt within the first solution is calculated to provide the support, after drying, with a alkaline earth metal concentration of less than 2.5, in other embodiments less than 2.0, and in other embodiments less than 1.7, and in other embodiments less than 1.5 wt % alkaline earth metal based upon the entire weight of the catalyst composition. In one or more embodiments, the concentration of the alkaline earth salt within the first solution is calculated to provide the support, after drying, with an alkaline earth metal concentration of 0%. In one or more embodiments, the concentration of the alkaline earth salt within the first solution is calculated to provide the support, after drying, with a alkaline earth metal concentration from about 0.5 to about 2.5, in other embodiments from about 0.7 to about 2.0, and in other embodiments from about 0.85 to about 1.7, and in other embodiments from about 1.0 to about 1.5 wt % alkaline earth metal based upon the entire weight of the catalyst composition. The foregoing wt % (s) are based upon the use of magnesium as the alkaline earth metal; where another alkaline earth metal is substituted for the magnesium, the foregoing wt % (s) will be adjusted for the difference in elemental weight of the different alkaline earth metal, keeping a molar equivalent to the moles of magnesium present in any given wt %. Stated another way, the foregoing represent the wt % (s) alkaline earth on the dried support following the first impregnation step.

In one or more embodiments, the concentration of the transition metal salt within the first solution is calculated to provide the support, after drying, with a transition metal concentration of greater than 0, in other embodiments greater than 0.5, and in other embodiments greater than 0.75, and in other embodiments greater than 1.0 wt % transition metal based upon the entire weight of the catalyst composition, which as described above includes the catalyst support, metals, and ligands or counter anions associated with any given metal additive. In these or other embodiments, the concentration of the transition metal salt within the first solution is calculated to provide the support, after drying, with a transition metal concentration of less than 2.5, in other embodiments less than 2.3, in other embodiments less than 2.2, and in other embodiments less than 2.0 wt % transition metal based upon the entire weight of the catalyst composition. In one or more embodiments, the concentration of the transition metal salt within the first solution is calculated to provide the support, after drying, with a transition metal concentration from about 0 to about 2.5, in other embodiments from about 0.5 to about 2.25, in other embodiments from about 0.75 to about 2.0, and in other embodiments from about 1.0 to about 2.0 wt % transition metal based upon the entire weight of the catalyst composition. Stated another way, the foregoing represent the wt % (s) transition metal on the dried support following the first impregnation step. The foregoing wt % (s) are based upon the use of manganese as the transition metal; where another transition metal is substituted for the manganese, the foregoing wt % (s) will be adjusted for the difference in elemental weight of the different transition metal, keeping a molar equivalent to the moles of manganese present in any given wt %.

Second Solution

In one or more embodiments, the second solution includes a copper salt, an alkaline earth metal salt, optionally a transition metal salt, and is substantially devoid of alkali metal. In particular embodiments, the second solution includes a copper salt, an alkaline earth metal salt, a transition metal salt, and is substantially devoid of alkali metal. In yet other particular embodiments, the second solution includes a copper salt, an alkaline earth metal salt, and is substantially devoid of an alkali metal and a transition metal.

In one or more embodiments, the concentration of the copper salt within the second solution is calculated to provide the product of the first impregnation, after drying, with an additional copper metal concentration of greater than 1.5, in other embodiments greater than 2.5, in other embodiments greater than 3.3, in other embodiments greater than 3.7, and in other embodiments greater than 4.0 wt % copper metal based upon the entire weight of the catalyst composition, which as described above includes the catalyst support, metals, and ligands or counter anions associated with any given metal additive. In these or other embodiments, the concentration of the copper salt within the second solution is calculated to provide the product of the first impregnation, after drying, with an additional copper metal concentration of less than 6.5, in other embodiments less than 5.5, and in other embodiments less than 5.0 wt % copper metal based upon the entire weight of the catalyst composition. In one or more embodiments, the concentration of the copper salt within the second solution is calculated to provide the product of the first impregnation, after drying, with an additional copper metal concentration of about 2.5 to about 6.5, in other embodiments from about 3.3 to about 5.5, and in other embodiments from about 4.0 to about 5.0 wt % copper metal based upon the entire weight of the catalyst composition.

The skilled person will appreciate that the additional metal (e.g. additional copper) imparted by the second impregnation step (i.e. from the second solution) can be calculated based upon the differential between the weight percentage of the metal based upon the entire weight of the catalyst composition after the first impregnation step and the weight percentage of the metal based upon the entire weight of the catalyst composition after the second impregnation step. For example, if it is assumed that the weight percentage of copper after the first impregnation step is 4.5 wt %, based upon the total weight of the catalyst composition after the first impregnation step, and that the weight percentage of copper after the second impregnation step is 8.5 wt %, based upon the total weight of the catalyst composition after the second impregnation step, then the total additional weight percent copper provided by the second impregnation step is 4.0 wt %, based upon the total weight of the catalyst composition after the second impregnation step.

In one or more embodiments, the concentration of the alkaline earth salt within the second solution is calculated to provide the product of the first impregnation, after drying, with an additional alkaline earth metal concentration of greater than 0.06, in other embodiments greater than 0.125, and in other embodiments greater than 0.18, in other embodiments greater than 0.20, in other embodiments greater than 0.22, and in other embodiments greater than 0.25 wt % alkaline earth metal based upon the entire weight of the catalyst composition, which as described above includes the catalyst support, metals, and ligands or counter anions associated with any given metal additive. In these or other embodiments, the concentration of the alkaline earth salt within the second solution is calculated to provide the product of the first impregnation, after drying, with an additional alkaline earth metal concentration of less than 1.5, in other embodiments less than 1.3, and in other embodiments less than 1.0 wt % alkaline earth metal based upon the entire weight of the catalyst composition. In one or more embodiments, the concentration of the alkaline earth salt within the second solution is calculated to provide the product of the first impregnation, after drying, with an additional alkaline earth metal concentration from about 0.06 to about 1.5, in other embodiments from about 0.18 to about 1.3, and in other embodiments from about 0.25 to about 1.0 wt % alkaline earth metal based upon the entire weight of the catalyst composition. The foregoing wt % (s) are based upon the use of magnesium as the alkaline earth metal; where another alkaline earth metal is substituted for the magnesium, the foregoing wt % (s) will be adjusted for the difference in elemental weight of the different alkaline earth metal, keeping a molar equivalent to the moles of magnesium present in any given wt %.

In one or more embodiments, the amount of alkaline earth metal imparted by the second impregnation step (i.e. from the second solution) is quantified, either alone or in combination with the parameters set forth above, based upon the amount of copper imparted by the second impregnation step. Stated another way, the invention can be defined based upon the molar ratio of alkaline earth metal (e.g. magnesium) to copper added in the second impregnation step. In one or more embodiments, the molar ratio of alkaline earth (e.g. magnesium) to copper added in the second impregnation step is greater than 0.19, in other embodiments greater than 0.22, in other embodiments greater than 0.24, in other embodiments greater than 0.26, and in other embodiments greater than 0.28. In one or more embodiments, the molar ratio of alkaline earth to copper added in the second impregnation step is from about 0.20 to about 0.50, in other embodiments is from about 0.22 to about 0.45, in other embodiments is from about 0.24 to about 0.40, and in other embodiments is from about 0.26 to about 0.36.

In one or more embodiments, the concentration of the transition metal salt within the second solution is calculated to provide the product of the first impregnation, after drying, with a transition metal concentration of greater than 0, in other embodiments greater than 0.5, and in other embodiments greater than 0.75, and in other embodiments greater than 1.0 wt % transition metal based upon the entire weight of the catalyst composition, which as described above includes the catalyst support, metals, and ligands or counter anions associated with any given metal additive. In these or other embodiments, the concentration of the transition metal salt within the second solution is calculated to provide the product of the first impregnation, after drying, with a transition metal concentration of less than 2.5, in other embodiments less than 2.3, in other embodiments less than 2.2, and in other embodiments less than 2.0 wt % transition metal based upon the entire weight of the catalyst composition. In one or more embodiments, the concentration of the transition metal salt within the second solution is calculated to provide the product of the first impregnation, after drying, with a transition metal concentration from about 0 to about 2.5, in other embodiments from about 0.5 to about 2.25, in other embodiments from about 0.75 to about 2.0, and in other embodiments from about 1.0 to about 2.0 wt % transition metal based upon the entire weight of the catalyst composition. The foregoing wt % (s) are based upon the use of manganese as the transition metal; where another transition metal is substituted for the manganese, the foregoing wt % s will be adjusted for the difference in elemental weight of the different transition metal, keeping a molar equivalent to the moles of manganese present in any given wt %.

As described above, the second solution is substantially devoid of alkali metal. This includes, by definition, being substantially devoid of alkali metal and any salts or other compounds including alkali metal. Substantially devoid, as it is used with respect to the alkali metal includes that amount or less of alkali metal that would not have an appreciable impact on the supported catalyst, especially with regard to practice of this invention. This includes a requirement that the amount of alkali metal in the second solution is lower than that amount that will have a deleterious impact on the stickiness of the supported catalyst produced according to this invention. In one or more embodiments, the second solution is devoid of alkali metal. In one or more embodiments, the concentration of any alkali metal, or alkali metal salt, within the second solution is less than that amount that would provide the support, after drying, with an additional alkali metal concentration of 0.5, in other embodiments 0.3, in other embodiments 0.1, or in other embodiments 0.05 wt % alkali metal.

As described above, in certain embodiments, the second solution is substantially devoid of transition metal. This includes, by definition, being substantially devoid of transition metal and any salts or other compounds including transition metal. Substantially devoid, as it is used with respect to the transition metal includes that amount or less of transition metal that would not have an appreciable impact on the supported catalyst, especially with regard to practice of this invention. In one or more embodiments, the second solution is devoid of transition metal. In one or more embodiments, the concentration of any transition metal, or transition metal salt, within the second solution of certain embodiments is less than that amount that would provide the support, after drying, with an additional transition metal concentration of 0.5, in other embodiments 0.3, in other embodiments 0.1, or in other embodiments 0.05 wt % transition metal.

INDUSTRIAL APPLICABILITY

In one or more embodiments, the catalyst compositions of the present invention are used in oxychlorination processes to convert ethylene to 1,2-dichloroethane. These processes are known as disclosed in, U.S. Pat. No. 5,292,703 and U.S. Publ. Nos. 2009/0054708, 2009/0298682, 2010/0274061, 2006/0129008, and 2004/0192978, which are incorporated herein by reference. In one or more embodiments, the process employs a fluid bed reactor. In particular embodiments, the process employs a baffled bed reactor.

In one or more embodiments, the oxychlorination catalyst of this invention can advantageously be used in oxychlorination processes where the molar ratio of oxygen to hydrogen chloride ($O_2/2HCl$) approaches a stoichiometric feed rate of 0.5. In one or more embodiments, the process operates at a molar ratio of oxygen to hydrogen chloride ($O_2/2HCl$) of less than 0.9, in other embodiments less than 0.7, in other embodiments less than 0.64, in other embodiments less than 0.62, in other embodiments less than 0.58, in other embodiments less than 0.57, in other embodiments less 0.56, in other embodiments less 0.55, in other embodiments less 0.54, in other embodiments less 0.53, in other embodiments less 0.52, in other embodiments less 0.51, in other embodiments less 0.50, in other embodiments less 0.48, in other embodiments less than 0.46, and in other embodiments less 0.44 without becoming deleteriously sticky.

This process can be carried out as a once through process wherein any unreacted ethylene is vented or otherwise removed, or in a recycle process wherein the unreacted ethylene is recycled back into the reactor. In the recycle process the ratio of HCl to ethylene will tend to be lower than 2 whereas in a once through process it will tend to approach or be closer to 2 thus resulting in a overall HCl to ethylene molar operating range of about 1 to about 2.

The catalyst compositions of the invention are highly efficient catalysts for the oxychlorination of ethylene to EDC. The reaction process temperatures vary from about 170° C. to about 260° C., from about 180° C. to about 250° C., and more specifically from about 190° C. to about 240° C. Reaction pressures vary from atmospheric to as high as about 200 psig. Contact times in the fluid bed and fixed bed catalysis can vary from about 5 seconds to about 50 seconds (contact time is defined here as the ratio of reactor volume taken up by the catalyst to the volumetric flow rate of the feed gases at the reactor control temperature and top pressure), and more preferably are from about 5 seconds to about 35 seconds. The ratio of the ethylene, HCl, and oxygen reactants, based on the moles of HCl fed to the reactor, range from about 1.0 to about 2.0 moles of ethylene and about 0.5 to about 0.9 mole of oxygen per 2.0 moles of HCl. As previously mentioned, modern oxychlorination processes attempt to operate within the stoichiometric ratio of about 1 to about 2 moles of HCl to 1 mole of ethylene.

TABLE I

Total Composition

| Metal | Low mol per kg catalyst | High mol per kg catalyst | Low Wt % | High Wt % |
|---|---|---|---|---|
| Alkali (Wt % based on K) | | | | |
| Embodiment 1 | 0.06 | 0.41 | 0.25 | 1.6 |
| Embodiment 2 | 0.13 | 0.38 | 0.50 | 1.5 |
| Embodiment 3 | 0.26 | 0.36 | 1.00 | 1.4 |
| Embodiment 4 | 0.27 | 0.33 | 1.05 | 1.3 |
| Alkali Earth (Wt % based on Mg) | | | | |
| Embodiment 1 | 0.10 | 1.23 | 0.25 | 3.0 |
| Embodiment 2 | 0.21 | 1.03 | 0.50 | 2.5 |
| Embodiment 3 | 0.31 | 0.93 | 0.75 | 2.25 |
| Embodiment 4 | 0.41 | 0.82 | 1.0 | 2.0 |
| Transition Metal (Wt % based on Mn) | | | | |
| Embodiment 1 | 0.00 | 0.46 | 0.00 | 2.5 |
| Embodiment 2 | 0.04 | 0.45 | 0.20 | 2.45 |
| Embodiment 3 | 0.07 | 0.43 | 0.40 | 2.35 |
| Embodiment 4 | 0.09 | 0.42 | 0.50 | 2.3 |
| Embodiment 5 | 0.14 | 0.40 | 0.75 | 2.2 |
| Embodiment 6 | 0.18 | 0.36 | 1.0 | 2.0 |

TABLE II

First Solution

| Metal | Low mol per kg catalyst | High mol per kg catalyst | Low Wt % | High Wt % |
|---|---|---|---|---|
| Alkali (Wt % based on K) | | | | |
| Embodiment 1 | 0.06 | 0.41 | 0.25 | 1.6 |
| Embodiment 2 | 0.13 | 0.38 | 0.5 | 1.5 |
| Embodiment 3 | 0.26 | 0.36 | 1.0 | 1.4 |
| Embodiment 4 | 0.27 | 0.33 | 1.05 | 1.3 |
| Alkali Earth (Wt % based on Mg) | | | | |
| Embodiment 1 | 0.21 | 1.03 | 0.5 | 2.5 |
| Embodiment 2 | 0.29 | 0.82 | 0.7 | 2.0 |
| Embodiment 3 | 0.35 | 0.7 | 0.85 | 1.7 |
| Embodiment 4 | 0.41 | 0.62 | 1.0 | 1.5 |
| Transition Metal (Wt % based on Mn) | | | | |
| Embodiment 1 | 0 | 0.46 | 0 | 2.5 |
| Embodiment 2 | 0.04 | 0.45 | 0.20 | 2.45 |
| Embodiment 3 | 0.07 | 0.43 | 0.40 | 2.35 |
| Embodiment 4 | 0.09 | 0.42 | 0.5 | 2.3 |
| Embodiment 5 | 0.14 | 0.40 | 0.75 | 2.2 |
| Embodiment 6 | 0.18 | 0.36 | 1.0 | 2.0 |

TABLE III

Second Solution

| Metal | Low mol per kg catalyst | High mol per kg catalyst | Low Wt % | High Wt % |
|---|---|---|---|---|
| Alkali Earth (Wt % based on Mg) | | | | |
| Embodiment 1 | 0.02 | 0.62 | 0.06 | 1.5 |
| Embodiment 2 | 0.05 | | 0.125 | |
| Embodiment 3 | 0.07 | 0.53 | 0.18 | 1.3 |
| Embodiment 4 | 0.10 | 0.41 | 0.25 | 1.0 |
| Transition Metal (Wt % based on Mn) | | | | |
| Embodiment 1 | 0 | 0.46 | 0 | 2.5 |
| Embodiment 2 | 0.04 | 0.45 | 0.20 | 2.45 |
| Embodiment 3 | 0.07 | 0.43 | 0.40 | 2.35 |
| Embodiment 4 | 0.09 | 0.42 | 0.5 | 2.3 |
| Embodiment 5 | 0.14 | 0.40 | 0.75 | 2.2 |
| Embodiment 6 | 0.15 | 0.36 | 1.0 | 2.0 |

In order to demonstrate the practice of the present invention, the following examples have been prepared and tested. The examples should not, however, be viewed as limiting the scope of the invention. The claims will serve to define the invention.

EXAMPLES

Catalysts are prepared by impregnating an alumina support with an aqueous solution of the desired metal chlorides using a two-step impregnation process, with the exception of Comparative Example 1, which is prepared using a single-step impregnation. The metal chloride solution is added to the alumina support as it is rotated and stirred in a ceramic dish. Each impregnation is carried out at room temperature. Subsequent to each impregnation, the ceramic dish containing the catalyst is placed over a steam bath for the initial drying phase (about 4 to 6 hours) and then heated up to 180° C. for the final drying phase (up to 16 hours).

The alumina support for the first set of Samples (i.e. Comparative Samples 1-3 and Inventive Samples 1 and 3-6) is purchased under the tradename Catalox SCCa 25/200 (Sasol), which is characterized by a pore volume of 0.40-0.50 mL/g, a surface area of 180-210 $m^2/g$, a particle size distribution where 0%-10% of the particles were smaller than 22 μm, and 905-100% of the particles were smaller than 125 μm. The alumina support for Inventive Sample 2 is purchased under the tradename Puralux SCCa 30/200 (Sasol), which is characterized by a pore volume of 0.40-0.50 mL/g, a surface area of 180-210 $m^2/g$, a particle size distribution where 0%-10% of the particles were smaller than 22 μm, and 905-100% of the particles were smaller than 125 μm. The volume of each solution employed corresponds to 90-115% of the pore volume of the support.

The aqueous solutions are prepared by employing one or more of the following metal salts: $CuCL_2 \cdot 2\ H_2O$, KCl, $MgCl_2 \cdot 6\ H_2O$, $MnCl_4 \cdot 4\ H_2O$. Table IV provides the details for the metal deposited on the support for each sample catalyst, and the skilled person can, without undue calculation or experimentation, determine the amount of metal salt to be added to a given solution in order to achieve the desired metal loading. For example, Comparative Example 3, which is prepared by a two-step impregnation, includes the preparation of a first solution by combining 9.73 g of $CuCL_2$, 2.48 g of KCl, 5.72 g of $MgCl_2$, and 1.79 g of $MnCl_4$, and dissolving the same in water to achieve 34.3 ml of water (which amount includes 9.76 g water of hydration associated with the salts). This solution is combined with 80.28 g of alumina. Upon drying, the finished catalyst, after the first impregnation step, includes the metal provided in Table IV, with the understanding that all of the metals adhere to the support. Following the first impregnation, a second solution is prepared by combining 9.94 g of of $CuCL_2$, and 1.37 g of $MgCl_2$, and dissolving the same in water to achieve 37.9 ml of water (which includes 4.22 g water of hydration associated with the salts). This solution is combined with 88.68 g of catalyst composition from the first step, and then is dried to provide a 100 g sample of catalyst composition having the metal adhered thereto as reported in Table IV; i.e. 100 g of the finished catalyst composition included 8.78 g Cu, 1.15 g K, 1.64 g Mg, and 0.44 g Mn, based on the weight of metal associated with the corresponding absorbed or adhered salts.

Table IV also provides the amount of metal included in the solution employed for the second impregnation, as well as the molar ratio of the Mg to Cu added in the second impregnation step. With reference again to Comparative Example 3, the skilled person will appreciate that 9.94 g of of $CuCl_2$ corresponds to 4.7 g Cu, and 1.37 g of $MgCl_2$ corresponds to 0.35 g Mg. These amounts provide a molar ratio of Mg to Cu of 0.19 (i.e. 0.0144/0.0740).

Still further, Table IV provides the amount of added metal imparted by the second impregnation step. Consistent with the explanation provided above, this amount is calculated based upon the differential between the weight percent of metal present on the support after the first impregnation step and the weight percent of metal present on the support after the second impregnation step and represented as a weight percent added amount based upon the total weight of the finished catalyst composition. For example, and with reference again to Comparative Example 3, the amount of Cu present within the catalyst composition after the first impregnation step is 4.6 wt %, and the amount of Cu present within the catalyst composition after the second impregnation step is 8.78 wt %, and therefore the differential is 4.18 wt % based upon the total weight of the total finished catalyst composition.

A laboratory-scale reactor is employed to analyse the usefulness of each catalyst composition. The laboratory-scale reactor includes a tubular glass reactor with an internal cross-sectional area of 2.78 $cm^2$. The reactor is operated at atmospheric pressure and is filled with an amount of catalyst leading to a fluidized bed height of 20±1.0 cm. The feed gas included 6.96 mmole/minute $N_2$, 4.87 mmole/minute of ethylene, 5.32 mmole/minute of HCl, and a variable $O_2$ to 2HCl molar feed ratio ranging from 0.6 down to 0.46. The reaction temperature is measured with a centered thermocouple in the fluidized bed and regulated on behalf of external electric heating. HCl in the feed and in the product gas is measured via titration. $N_2$, $C_2H_4$, $O_2$, $CO_x$, and chlorinated hydrocarbons are measured via GC (HP 6890 Series; Column types—1) Vocol glass capillary column (60 meter; 0.75 mm ID; 1.5 micron film thickness. 2) $^{80}/_{100}$ Porapak N column (12 foot×⅛ inch, stainless steel). 3) $^{60}/_{80}$ molecular sieve, 5 angstrom (6 foot×⅛ inch); Detectors—2 TCD's. Detector B (Vocol column) Detector A (mol sieve/Porapak); One TCD is used to detect light gases, such as $O_2$, $N_2$, and CO from the molecular sieve column, and heavier gases, such as $CO_2$ and ethylene as well as lighter chlorinated hydrocarbons such as vinyl chloride and ethyl chloride from the Porapak column. A second TCD is used to detect the remaining heavier chlorinated hydrocarbons from the Vocol column starting with chloroform, including EDC and other heavier chlorinated by-products.).

Based on the analytics and the feed gas amounts, the HCl conversion, the ethylene conversion, the EDC selectivity and the selectivity of the different oxidized and chlorinated by-products is calculated. The sticking resistance is evaluated by gradually lowering the oxygen to 2HCl ratio at a given operating temperature to the point where visual agglomerations of the catalyst, fluctuations in the differential pressure or sudden changes in selectivity occurs. More specifically, the observation of catalyst stickiness is achieved both visually and by measuring the change in the pressure drop across the fluidized bed using a differential pressure metering device. Under typical fluidization or non-sticky conditions the catalyst is moving freely and smoothly in the reactor with a fairly constant effluent gas exit rate where gaseous pockets or bubbles observed within the bed are of small diameter and minimal in quantity. This visual observation corresponds to a measured differential pressure that contained very little noise or fluctuation in the differential pressure value that is observed during good fluidization or non-sticky conditions.

As the catalyst becomes sticky, the fluid-bed height increases by up to 10% of the normal bed height prior to fluidization failure or the onset of severe catalyst stickiness. At the failure point, slugging of the catalyst bed is observed where large gas pockets are formed and the catalyst is no longer fluidizing well but instead is showing particle clustering or agglomeration. Additionally, the pressure differential observed across the fluid-bed becomes unstable resulting in larger than normal swings relative to when operating under non-sticky conditions. A typical differential pressure reading may vary by +/−1 mbar under non-sticky operating conditions. This "low noise" pressure reading relates to good fluidization or non-sticky operating conditions. When the differential pressure reading consistently varies by more than +/−3 mbar, this "high noise" condition represents the point of poor fluidization or catalyst stickiness.

TABLE IV

| Sample No. | Comparative | | | Inventive | | | | | |
|---|---|---|---|---|---|---|---|---|---|
| | 1 | 2 | 3 | 1 | 2* | 3 | 4 | 5 | 6 |
| Targeted Composition (Step 1) | | | | | | | | | |
| Cu (wt %) | 8.7 | 4.3 | 4.6 | 4.2 | 4.2 | 4.6 | 4.4 | 4.6 | 4.5 |
| K (wt %) | 0.03 | 1.1 | 1.3 | 1.11 | 1.11 | 1.2 | 1.2 | 1.3 | 1.25 |
| Mg (wt %) | 1.15 | 1.3 | 1.46 | 1.31 | 1.30 | 1.5 | 1.2 | 1.46 | 1.3 |
| Mn (wt %) | 0.2 | 0.8 | 0.5 | 0.8 | 0.8 | 0.5 | 0.6 | 0.5 | 1.0 |
| Targeted Composition (Step 2) | | | | | | | | | |
| Cu (wt %) | — | 1.81 | 4.7 | 4.2 | 4.2 | 4.6 | 4.7 | 4.7 | 4.7 |
| Mg (wt %) | — | — | 0.35 | 0.4 | 0.4 | 0.45 | 0.5 | 0.5 | 0.5 |
| Mg:Cu (Molar Ratio) | N/A | N/A | 0.19 | 0.25 | 0.25 | 0.26 | 0.28 | 0.28 | 0.28 |

TABLE IV-continued

|  | Comparative | | | Inventive | | | | | |
|---|---|---|---|---|---|---|---|---|---|
| Sample No. | 1 | 2 | 3 | 1 | 2* | 3 | 4 | 5 | 6 |
| Total Composition (Finished) | | | | | | | | | |
| Cu (wt %) | 8.7 | 5.95 | 8.78 | 7.96 | 7.96 | 8.67 | 8.58 | 8.75 | 8.66 |
| K (wt %) | 0.03 | 1.06 | 1.15 | 0.99 | 0.99 | 1.06 | 1.06 | 1.15 | 1.10 |
| Mg (wt %) | 1.15 | 1.25 | 1.64 | 1.57 | 1.56 | 1.78 | 1.56 | 1.79 | 1.65 |
| Mn (wt %) | 0.2 | 0.77 | 0.44 | 0.72 | 0.72 | 0.44 | 0.52 | 0.44 | 0.88 |
| Added Metal | | | | | | | | | |
| Cu (wt %) | N/A | 1.65 | 4.18 | 3.76 | 3.76 | 4.07 | 4.18 | 4.15 | 4.16 |
| Mg (wt %) | N/A | N/A | 0.18 | 0.26 | 0.26 | 0.28 | 0.36 | 0.33 | 0.35 |
| Experimental Results | | | | | | | | | |
| Sticky (Y/N) | Y | Y | Y | N | N | N | N | N | N |
| Meets or exceeds 99.5% HCl Conversion and 98.0% EDC Selectivity (Y/N) | N | Y | Y | Y | Y | Y | Y | Y | Y |
| Meets or exceeds 99.5% HCl Conversion and 99.0% EDC Selectivity (Y/N) | N | Y | Y | Y | Y | Y | Y | Y | Y |

Various modifications and alterations that do not depart from the scope and spirit of this invention will become apparent to those skilled in the art. This invention is not to be duly limited to the illustrative embodiments set forth herein.

What is claimed is:

1. A process for producing a supported catalyst for the oxychlorination of ethylene to 1,2-dichloroethane, the process comprising the steps of:
   (i) impregnating, within a first step, an alumina support with a first aqueous solution including copper, an additional transition metal selected from the group consisting of manganese and rhenium, an alkali metal, and an alkaline earth metal, to thereby form a first catalyst component, wherein the first aqueous solution provides the alumina support with an alkali metal concentration of greater than 0.5 weight percent based upon the entire weight of the supported catalyst, wherein the first aqueous solution provides the alumina support with a copper concentration of from greater than 4.0 weight percent to less than 6.5 weight percent based upon the entire weight of the supported catalyst; and
   (ii) impregnating, within a subsequent step, the first catalyst component with a second aqueous solution including copper, alkaline earth metal, and optionally additional alkali metal, to thereby form the supported catalyst, wherein the second aqueous solution includes an alkaline earth metal to copper molar ratio of greater than 0.19, wherein the concentration of any additional alkali metal within the second aqueous solution is an amount that would provide the alumina support with an additional alkali metal concentration of less than 0.3 weight percent additional alkali metal based upon the entire weight of the supported catalyst, wherein the second aqueous solution provides the alumina support with an additional copper concentration of from greater than 4.0 weight percent to less than 6.5 weight percent based upon the entire weight of the supported catalyst.

2. The process of claim 1, wherein the second aqueous solution includes an alkaline earth metal to copper molar ratio of from 0.20 to 0.50.

3. The process of claim 1, wherein the supported catalyst after (ii) includes greater than 1.0 weight percent alkali metal based upon the entire weight of the supported catalyst.

4. The process of claim 1, wherein the supported catalyst after (ii) includes from 1.05 to 1.6 weight percent alkali metal based upon the entire weight of the supported catalyst.

5. The process of claim 1, wherein the second aqueous solution is devoid of alkali metal.

6. In an oxychlorination process of the type where ethylene is converted to 1,2-dichloroethane in the presence of a supported copper catalyst, the improvement comprising: the use of a supported catalyst prepared by (i) impregnating, within a first step, an alumina support with a first aqueous solution including copper, an additional transition metal selected from the group consisting of manganese and rhenium, an alkali metal, and an alkaline earth metal, to thereby form a first catalyst component, wherein the first aqueous solution provides the alumina support with an alkali metal concentration of greater than 0.5 weight percent based upon the entire weight of the supported catalyst, wherein the first aqueous solution provides the alumina support with a copper concentration of from greater than 4.0 weight percent to less than 6.5 weight percent based upon the entire weight of the supported catalyst; and (ii) impregnating, within a subsequent step, the first catalyst component with a second aqueous solution including copper, alkaline earth metal, and optionally additional alkali metal, to thereby form the supported catalyst, wherein the second aqueous solution includes an alkaline earth metal to copper molar ratio of greater than 0.19, where the concentration of any additional alkali metal within the second aqueous solution is an amount that would provide the alumina support with an additional alkali metal concentration of less than 0.3 weight percent_based upon the entire weight of the supported catalyst, wherein the second aqueous solution provides the alumina support with an additional copper concentration of from greater than 4.0 weight percent to less than 6.5 weight percent based upon the entire weight of the supported catalyst.

7. The process of claim 6, wherein the oxychlorination process is conducted within a fluid-bed reactor.

8. The process of claim 6, wherein the fluid bed reactor is a baffled-bed reactor.

9. The process of claim 6, wherein the supported catalyst after (ii) includes from about 0.25 to about 3.0 weight percent alkaline earth metal based upon the entire weight of the supported catalyst.

10. The process of claim 6, wherein the supported catalyst includes from about 0.5 to about 2.25 weight percent transition metal based upon the entire weight of the supported catalyst.

11. The process of claim 6, wherein the alkaline earth metal is magnesium.

12. The process of claim 6, wherein the alkali metal is potassium.

13. The process of claim 12, wherein the alkaline earth metal is magnesium.

14. The process of claim 6, wherein the additional transition metal is manganese.

15. An oxychlorination process comprising the step of: converting ethylene to 1,2-dichloroethane in the presence of a supported catalyst, oxygen, and hydrogen chloride, where the supported catalyst is produced by:
  (i) impregnating, within a first step, an alumina support with a first aqueous solution including copper, an additional transition metal selected from the group consisting of manganese and rhenium, an alkali metal, and an alkaline earth metal, to thereby form a first catalyst component, wherein the first aqueous solution provides the first catalyst component with an alkali metal concentration of greater than 0.5 weight percent based upon the entire weight of the supported catalyst, wherein the first aqueous solution provides the alumina support with a copper concentration of from greater than 4.0 weight percent to less than 6.5 weight percent based upon the entire weight of the supported catalyst; and
  (ii) impregnating, within a subsequent step, the first catalyst component with a second aqueous solution including copper, alkaline earth metal, and optionally additional alkali metal, to thereby form the supported catalyst, wherein the second aqueous solution includes an alkaline earth metal to copper molar ratio of greater than 0.19, wherein the concentration of any additional alkali metal within the second aqueous solution is an amount that would provide the alumina support with an additional alkali metal concentration of less than 0.3 weight percent based upon the entire weight of the supported catalyst, wherein the second aqueous solution provides the alumina support with an additional copper concentration of from greater than 4.0 weight percent to less than 6.5 weight percent based upon the entire weight of the supported catalyst.

* * * * *